United States Patent [19]

Callewaert et al.

[11] Patent Number: 4,604,357

[45] Date of Patent: Aug. 5, 1986

[54] ANTIMICROBIAL DISINFECTING URINAL BLOCK MEANS AND METHODS OF USE

[75] Inventors: Denis M. Callewaert, Oxford; Earl J. Braxton, Utica, both of Mich.

[73] Assignee: Enzymes of America, Utica, Mich.

[21] Appl. No.: 600,141

[22] Filed: Apr. 13, 1984

[51] Int. Cl.$^4$ ............................................. C12N 9/72
[52] U.S. Cl. .................................. 435/215; 424/14; 530/834
[58] Field of Search ................ 435/215; 4/449, 459, 4/231, 309; 424/14; 260/112 R

[56] References Cited

U.S. PATENT DOCUMENTS

| | | |
|---|---|---|
| 3,375,159 | 3/1968 | Batton ..................................... 4/231 |
| 3,405,454 | 10/1968 | Zeff ........................................ 4/449 |
| 3,529,309 | 9/1970 | Leavitt et al. ........................... 4/231 |
| 3,668,717 | 6/1972 | Curran ..................................... 4/231 |
| 3,755,083 | 8/1973 | Novak ................................... 435/215 |
| 4,096,593 | 6/1978 | Vlahakis ................................. 4/231 |
| 4,258,030 | 3/1981 | Sasaki et al. ........................ 435/215 |
| 4,285,077 | 8/1981 | Braxton ................................. 4/449 |
| 4,557,863 | 12/1985 | Callewaert et al. ............ 260/112 R |

Primary Examiner—Ronald W. Griffin
Attorney, Agent, or Firm—Krass & Young

[57] ABSTRACT

The invention relates to disinfectant urinal block means useful for collection of pooled urine and method of using the block means to provide in service release, of an antimicrobial agent component from the block means into the pool for effective inhibition of bacterial growth and consequent enzymatic degradation of wanted proteins contained in the pool.

8 Claims, No Drawings ic Field

The invention relates to disinfectant urinal block means useful for collection of pooled urine over an extended period of collection. More particularly, the invention relates to such block means and method of use comprising a water-soluble antimicrobial component for in service incremental release of the component from the block means into the collected pool for effective inhibition of microbial growth and consequent degradation of wanted proteins in the pool during the period of collection.

2. Background Art

Mammalian urine contains small percentages of a variety of proteins and especially enzymes which have commercial value, usually as pharmaceuticals. For example, the enzyme urokinase, which is present in trace percentages in human urine, is widely used as a fibrinolytic agent and in connection with treatment for cancer because of its ability to dissolve the fibrin growths which sometimes sheath tumor cells. Most of the commercial supply of urokinase is now derived from urine by the collection of urine from paid donors who regularly visit central collection stations. Within a few hours of being collected the urine is transported to a central processing station where the large protein molecules of interest such as urokinase or other commercially useful proteins are isolated. U.S. Pat. No. 3,755,083 discloses a process of this type.

Urokinase and other urinary enzymes rapidly degenerate at normal collection temperatures so that it is necessary to process the urine as soon as possible after it is collected. The resulting collection and processing costs and the low percentage of urokinase contained in urine result in a very high unit cost, severely limiting pharmaceutical use of the material.

SUMMARY AND DETAILED DESCRIPTION OF THE INVENTION

The present invention is directed to a novel type of disinfectant urinal block means that is useful when installed in a urinal for collection of pooled urine, especially human urine, for later isolation of its content of valuable urinary proteins, enzymes and peptides having application, e.g., as pharmaceutically active agents in human or veterinary medicine. The urinal block means of the invention is an antimicrobial disinfectant urinal block means having an operative service life of given duration for exposure to air and to intermittent urine streams. The block means according to the invention contains (1) a hydrophilic component comprising an antimicrobial agent adapted in operation to be leached ratably by exposure to intermittent urine streams and (2) a water-insoluble hydrophobic component adapted in operation to sublime ratably to the air, the respective rates of leaching and subliming during the service life being chosen such that the leaching of antimicrobial agent from the block means into the pooled urine is sufficient to provide an inhibitor concentration effectively inhibiting microbial growth and consequent degradation of wanted proteins contained in the pool. The hydrophilic component of the invention is any suitable water-soluble form of an antimicrobial agent or general protease inhibitor, that is to say, a substance or mixture of substances that serves to inhibit the bacterial degradation of urinary protein in the urine pool as by elimination of bacterial growth on urinary protein such as urokinase, kallikrein, erythropoetin, urogastrone, and the like. A preferred inhibitor, for purposes of the invention, is one that inhibits microbial degradation of the human plasminogen activator urokinase. For this purpose, one may use any suitable water-soluble antibacterial substance that is effective in preventing or inhibiting bacterial growth and consequent enzymatic degradation of the desired protein in the urine pool. Preferred inhibitors are one or more water-soluble salts of pyrithione, preferably sodium pyrithione (also known as sodium omadine or 2-pyridinethiol 1-oxide, sodium salt), or a water-soluble azide salt, preferably sodium azide.

The hydrophobic component of the invention is any suitable water-insoluble aromatic hydrocarbon or halogenated hydrocarbon or mixture thereof that sublimes continuously in air at ambient room temperatures ranging, for example, from about 50 to about 100 degrees F. A preferred hydrophobic component, for purposes of the invention, is p-dichlorobenzene or naphthalene.

The urinal block means of the invention can take any suitable solid or porous physical form which may be conventional such as a single three-dimensional rectilinear block or rounded or otherwise shaped pellet form. The block means can be a homogeneous mixture of the hydrophobic and hydrophilic components or it can be laminated or formed with the hydrophilic component as small particulates spaced or distributed uniformly throughout a matrix of the hydrophobic component. The invention contemplates that for collection of the urine pool the urinal block means is installed in a urinal of the type where it is exposed to air and intermittent urine streams but not exposed to flushing water, as for example a portable toilet having an unflushed urinal with gravity feed through a flow line first to an adsorbent chamber and then to a holding tank such as that described in the patent to Braxton, U.S. Pat. No. 4,285,077.

The hydrophilic and hydrophobic components may contain a suitable deodorizing or sanitizing substance or other excipient or diluent. As contemplated, when the urinal block means of the invention is exposed to the air (as when installed on a mesh screen in the flow line of a portable toilet such as described above), the hydrophobic component undergoes continuous sublimation while so exposed at a rate depending on the air temperature. Thus, the content of aromatic hydrocarbon in the block means is gradually diminished over the period of the operative service life of the block means. When the urinal block means is exposed to the intermittent urine streams, the latter serve to leach any of the hydrophilic component that is exposed by the mentioned continuing sublimation of the hydrophobic component. In other words, the release of the water-soluble component is a discontinuous slow release coinciding with the intermittent urine streams occurring during the predetermined service life of the urinal block means. Such release of the antimicrobial component, for purposes of the invention, is important because as the urine pool increases, it requires to a corresponding extent an increasing inhibition of bacterial action. The relative content and quantities of the hydrophilic and hydrophobic components in the block means are subject to considerable variation depending on the operating conditions. For example, for a urine pool of about 80 liters and a service life at room temperature of about 4 days, one may use in a preferred form a urinal block rectilinear in shape weighing about 20 g. and containing by weight about 5 to about 10% antimicrobial component or agent and about 90 to about 95% hydrophobic component, preferably sodium pyrithione and p-dichlorobenzene. Equivalently, four of such blocks can be used each weighing about 5 g. Advantageously, the urinal block provides several unexpected features. The block is usefully depleted by sublimation of its hydrophobic component such that its hydrophilic content is progressively exposed or made accessible for intermittent leaching in the amounts required by the pooled urine. Also, the collection time without substantial loss of valuable protein and enzyme content is extended for a prolonged period enabling economic collection and service practices.

The invention in another aspect relates to the method of minimizing urine protein degradation occurring during the collection of urine employing the urinal block means described above. The method comprises the step of collecting urine to which the block means is exposed in a common pool together with antimicrobial agent that is leached from the block means for a time not longer than the expiration of the useful life of the antimicrobial agent, preferably not longer than about four days of collection time.

The invention is illustrated and the best mode of carrying out the same is set forth in the following examples.

EXAMPLE 1

Para-dichlorobenzene (95 parts by weights; m.p., ca. 54 degrees C.) is melted and blended with sodium omadine (5 parts) to provide a homogeneous mixture. The mixture is cooled until solidified, and blocks of the solidified mixture are made, each weighing about 5 grams.

For collection purposes in a non-flushing urinal, each block supported in air on a screen and exposed to intermittent urine flow is sufficient to provide at room temperature continuous sublimation of the hydrophobic component (i.e., para-dichlorobenzene) and controlled intermittent release of the hydrophilic component (sodium omadine). The operative service life using four 5-gram blocks is about 96 hours or about 24 hours per 5-gram block. Assay of the 4-day collected urine pool indicates that microbial growth and degradation of urokinase are substantially completely inhibited, by comparison with the average urokinase level of freshly collected unstored aliquots.

EXAMPLE 2

The procedure of Example 1 is repeated except that naphthalene (m.p., 80 degrees C.) is substituted for para-dichlorobenzene, in the same amount.

EXAMPLE 3

The procedure of Example 1 is repeated except that sodium azide in crystal form is substituted for sodium omadine so that on blending the crystalline particles become dispersed in the melt. On cooling and solidification, the solidified mixture is partitioned into blocks of equal size and weight (5 g.) each containing a uniform dispersion of sodium azide crystals, suitable for collection of pooled urine, as described.

The embodiments in which an exclusive property or privilege is claimed are defined as follows:

1. A method of minimizing urine protein degradation occurring during the collection of pooled urine employing as urinal block means a hydrophilic water-leachable antimicrobial agent adapted in operation to be leached ratably by exposure to intermittent urine streams that is distributed in a matrix of water-insoluble hydrophobic component adapted in operation to sublime ratably to the air, the antimicrobial agent being partly leachable when exposed to urine streams and partly leachable only when and as the matrix sublimes away from the block, the respective rates of leaching and subliming during the service life being chosen such that the antimicrobial agent progressively exposed by said subliming and leaching of the thus exposed antimicrobial agent from the block means into the pooled urine is sufficient to provide an inhibitor concentration effectively inhibiting microbial growth and consequent degradation of wanted proteins contained in the pool, the method comprising the steps of installing the block means in a urinal at a location such that the block means is exposed to air and intermittent urine streams but is not exposed to flushing water, allowing the matrix to sublime and progressively expose the water-leachable antimicrobial agent while further allowing said agent to be protected from exposure to flushing water and to be exposed to urine streams and released to the pool in a discontinuous slow release coinciding with the intermittent streams, and collecting urine to which the block means is exposed in a common pool together with an antimicrobial agent that is leached from the block means for a time not longer than the expiration of the useful life of the antimicrobial agent.

2. The method according to claim 1 where the hydrophilic component comprises a water soluble salt of pyrithione.

3. The method according to claim 1 where the hydrophilic component comprises sodium pyrithione.

4. The method according to claim 1 where the hydrophilic component comprises sodium azide.

5. The method according to claim 1 where the hydrophobic component comprises p-dichlorobenzene.

6. The method according to claim 1 where the block means consists of a homogeneous mixture of sodium pyrithione and p-dichlorobenzene.

7. The method according to claim 6 where the block means is by weight about 5 to about 10% sodium pyrithione and about 90 to about 95 p-dichlorobenzene.

8. The method according to claim 1 employing a quantity of antimicrobial agent that when leached at the rate of about 1 to about 2 grams per 80 liters is sufficient for a service time of about 4 days.

* * * * *

UNITED STATES PATENT AND TRADEMARK OFFICE
CERTIFICATE OF CORRECTION

PATENT NO.   : 4,604,357

DATED        : August 5, 1986

INVENTOR(S)  : Dennis M. Callewaert et al.

It is certified that error appears in the above-identified patent and that said Letters Patent is hereby corrected as shown below:

Column 4, line 56 "95" should be --95%--.

Signed and Sealed this

Fourth Day of November, 1986

[SEAL]

*Attest:*

DONALD J. QUIGG

*Attesting Officer*      *Commissioner of Patents and Trademarks*